United States Patent
Jones et al.

(10) Patent No.: US 10,273,203 B2
(45) Date of Patent: Apr. 30, 2019

(54) DEUTERATED 3-METHANESULFONYLPROPIONITRILE

(71) Applicant: Olatec Therapeutics LLC, New York, NY (US)

(72) Inventors: Gerald S. Jones, Norwood, MA (US); Scott A. Goodrich, Stoughton, MA (US); Joseph P. St. Laurent, Lakeville, MA (US)

(73) Assignee: Olatec Therapeutics LLC, New York, NY (US)

( * ) Notice: Subject to any disclaimer, the term of this patent is extended or adjusted under 35 U.S.C. 154(b) by 0 days.

(21) Appl. No.: 15/945,542

(22) Filed: Apr. 4, 2018

(65) Prior Publication Data

US 2018/0290971 A1    Oct. 11, 2018

Related U.S. Application Data

(60) Provisional application No. 62/484,177, filed on Apr. 11, 2017.

(51) Int. Cl.
| | | |
|---|---|---|
| *C07C 317/28* | (2006.01) |
| *C07C 315/04* | (2006.01) |
| *C07C 315/02* | (2006.01) |

(52) U.S. Cl.
CPC .......... *C07C 317/28* (2013.01); *C07C 315/02* (2013.01); *C07C 315/04* (2013.01); *C07B 2200/05* (2013.01); *C07B 2200/07* (2013.01)

(58) Field of Classification Search
CPC .... C07C 317/28; C07C 315/02; C07C 315/04
See application file for complete search history.

(56) References Cited

U.S. PATENT DOCUMENTS

| 8,476,316 B2 | 7/2013 | St. Laurent |
| 8,802,885 B2 | 8/2014 | St. Laurent et al. |

*Primary Examiner* — Shawquia Jackson
(74) *Attorney, Agent, or Firm* — Perkins Coie LLP; Viola T. Kung

(57) ABSTRACT

The present invention relates to purified compounds of 3-methanesulfonylpropionitrile, in which at least one of the hydrogen, oxygen, sulfur, and nitrogen atoms is substituted with a respective isotope that includes, but not limited to $^2$H (deuterium), $^3$H (tritium), $^{13}$C, $^{14}$C, $^{15}$N, $^{17}$O, $^{18}$O, and $^{35}$S. The purified compound has at least 90% purity. Preferred compounds are deuterated 3-methanesulfonylpropionitriles.

8 Claims, No Drawings

DEUTERATED 3-METHANESULFONYLPROPIONITRILE

This application claims the benefit of U.S. Provisional Application No. 62/484,177, filed Apr. 11, 2017, which is incorporated herein by reference in its entirety.

FIELD OF THE INVENTION

The present invention relates to deuterated 3-methanesulfonylpropionitrile, or its pharmaceutically acceptable salts. The compound is purified to ≥90% purity. The present invention also relates to a pharmaceutical composition comprising the compound and a pharmaceutically acceptable carrier.

BACKGROUND OF THE INVENTION

Inflammation is a process by which microbes or tissue injury induce the release of cytokines and chemokines from various cell types producing increased blood vessel permeability, upregulation of endothelial receptors, and thus increased egress of various cells of the innate and adaptive immune system which enter surrounding tissue and grossly produce the classical picture of inflammation, i.e. redness, swelling, heat and pain.

Inflammation is a localized reaction of live tissue due to an injury, which may be caused by various endogenous and exogenous factors. The exogenous factors include physical, chemical, and biological factors. The endogenous factors include inflammatory mediators, antigens, and antibodies. Endogenous factors often develop under the influence of an exogenous damage. An inflammatory reaction is often followed by an altered structure and penetrability of the cellular membrane. Endogenous factors, namely, mediators, antigens, and autogens define the nature and type of an inflammatory reaction, especially its course in the zone of injury. In the case where tissue damage is limited to the creation of mediators, an acute form of inflammation develops. If immunologic reactions are also involved in the process, through the interaction of antigens, antibodies, and autoantigens, a long-term inflammatory process will develop. Various exogenous agents, for example, infection, injury, radiation, also provide the course of inflammatory process on a molecular level by damaging cellular membranes which initiate biochemical reactions.

Connective tissues are subjected to a constant barrage of stress and injury. Acute or chronic impacts and the natural progression of various degenerative diseases all produce painful inflammation in joint regions, such as the neck, back, arms, hips, ankles and feet. These afflictions are common and often debilitating.

U.S. Pat. No. 8,476,316 discloses that 3-methanesulfonylpropionitrile is effective for treating inflammation, inflammatory-related disorders, and/or pain.

DETAILED DESCRIPTION OF THE INVENTION

Definitions

"Pharmaceutically acceptable salts," as used herein, are salts that retain the desired biological activity of the parent compound and do not impart undesired toxicological effects. Pharmaceutically acceptable salt forms include various crystalline polymorphs as well as the amorphous form of the different salts. The pharmaceutically acceptable salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4+$ (wherein X is $C_{1-4}$).

"Solvates," as used herein, are addition complexes in which the compound is combined with an acceptable co-solvent in some fixed proportion. Co-solvents include, but are not limited to, water, acetic acid, ethanol, and other appropriate organic solvents.

Purified Compound

The present invention is directed to a compound of 3-methanesulfonylpropionitrile, or a pharmaceutically acceptable salt thereof, in which at least one of the hydrogen, oxygen, sulfur, and nitrogen atoms is substituted with a respective isotope that includes, but not limited to, $^2H$ (deuterium), $^3H$ (tritium), $^{13}C$, $^{14}C$, $^{15}N$, $^{17}O$, $^{18}O$, and $^{35}S$; preferably substituted with a non-radioactive or stable isotope that includes $^2H$ (deuterium), $^{13}C$, $^{15}N$, $^{17}O$, or $^{18}O$; more preferably substituted with $^2H$ (deuterium).

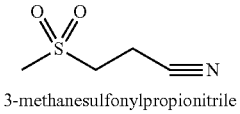

3-methanesulfonylpropionitrile

In a preferred embodiment, one or more hydrogens of 3-methanesulfonylpropionitrile are substituted with $^2H$ (deuterium). For example, 3-methanesulfonylpropionitrile can be substituted by 1, 2, 3, 4, 5, 6, or 7 deuterium atoms. The following three compounds illustrate the substitution of 3-methanesulfonylpropionitrile by 3, 4, and 7 deuteriums (D).

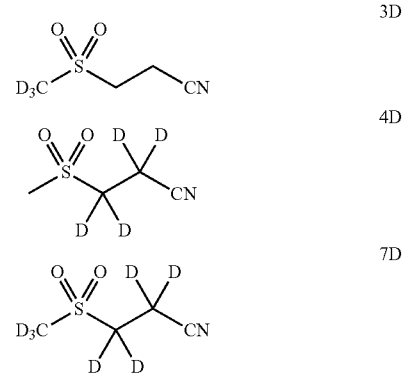

Compound 3D, 3-(trideuteriomethyl)sulfonylpropionitrile (3) can be prepared by Scheme 1 as shown below.

Scheme 1

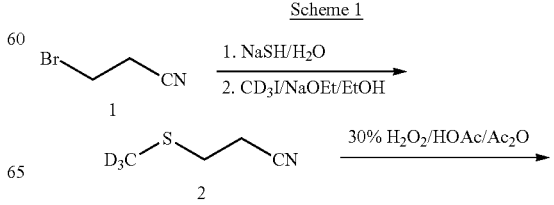

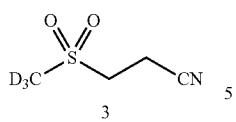

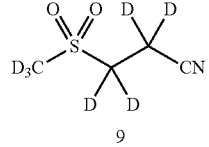

Treatment of 3-bromopropionitrile (1) with an aqueous solution of sodium hydrosulfide (NaSH) gives the corresponding thiol, which is alkylated with iodomethane-$d_3$ ($CD_3I$) under basic conditions. The resultant sulfide (2) is oxidized with hydrogen peroxide to produce 3-methanesulfonylpropionitrile-$d_3$.

Compound 4D (7) can be prepared by Scheme 2 as shown below.

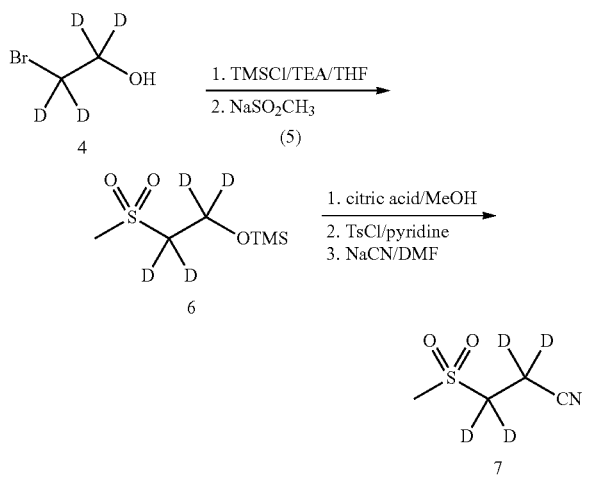

Commercially available 2-bromoethanol-1,1,2,2-$d_4$ (4) is first protected as a trimethylsilyl ether, or protected by other protecting group. The protected compound is used to alkylate sodium methylsulfinate (5). The resultant sulfone (6) is first deprotected under acidic conditions, then converted to tosylate, which undergoes subsequent displacement with cyanide ion to produce 3-methanesulfonylpropionitrile-$d_4$ (7).

Compound 7D (9) can be prepared by Scheme 3 as shown below.

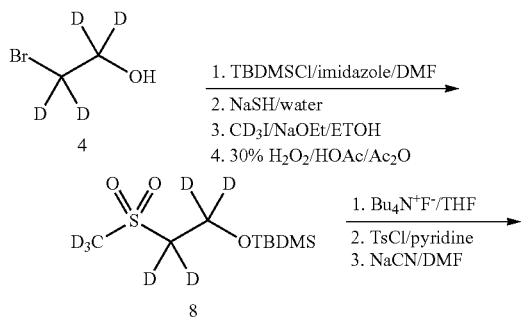

2-Bromoethanol-1,1,2,2-$d_4$ (4) is first protected as the t-butyldimethylsilyl ether, then treated with an aqueous solution of sodium hydrosulfide (NaSH). Further synthetic elaboration, as shown in Scheme 1 (alkylation with $CD_3I$; oxidation with $H_2O_2$), gives protected sulfone 8. Deprotection and subsequent synthetic elaboration, as shown in Scheme 2 (tosylation; substitution), produce fully deuterated 3-methanesulfonylpropionitrile-$d_7$ (9).

The compound of the present invention preferably has a purity of at least 85%, 90%, 95%, 97%, 98%, or 99%.

The deuterated 3-methanesulfonylpropionitrile compounds are useful as analytical tools. For example, the compounds can be used as an analytical reference standard for chromatographic analyses such as HPLC and GC.

Selective replacement of hydrogen atoms with deuterium (deuteration) yields a compound similar to the non-deuterated parent compound, yet it may result in changes, sometimes negligible, in physicochemical properties such as hydrophobicity, and acidity/basicity of ionizable functional groups.

Moreover, deuteration can, in certain instances, positively impact the metabolic fate of a physiologically active compound resulting in improved safety and/or efficacy. The primary deuterium isotope effect, i.e., a slower rate for carbon-deuterium (C-D) covalent bond cleavage relative to the corresponding C—H bond, may potentially result in reduced rates of metabolism and metabolic switching, where the ratio of metabolites is changed, thereby affecting the pharmacokinetics of a drug that is metabolized by pathways involving C—H bond scission.

Deuterium isotope effects on noncovalent interactions between molecules, including hydrogen bonding and ionic and van der Waals interactions may occur. These binding isotope effects may contribute to the overall pharmacodynamic activity of a deuterated drug.

The deuterated 3-methanesulfonylpropionitrile compounds may provide improved pharmacokinetic properties (e.g., longer half-life) from those of 3-methanesulfonylpropionitrile. The deuterated 3-methanesulfonylpropionitrile compounds may have improved physical properties and may have a better stability; e.g., the kinetic isotope effect may retard $E_2$ elimination.

Theoretically, a reduced rate of metabolism for compound 3 relative to the non-deuterated analogue may occur, if the latter is susceptible to the type of oxidative metabolic process shown below:

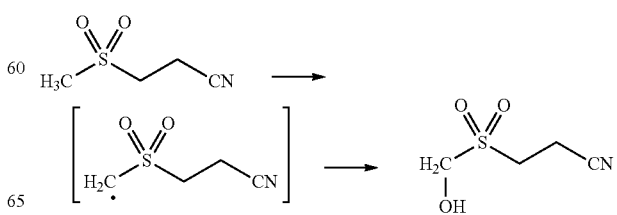

Likewise, compounds 7 and 9 may be intrinsically more stable than the non-deuterated analogue, if the latter is prone to the elimination reaction shown below:

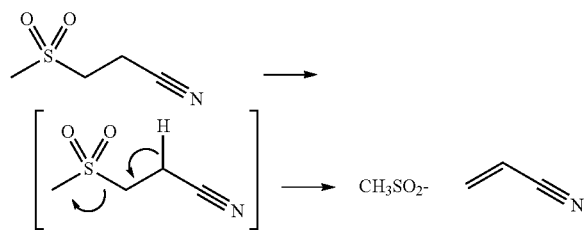

Pharmaceutical Compositions

The present invention is also directed to a pharmaceutical composition comprising a pharmaceutically acceptable carrier and the pharmaceutically acceptable salts, or solvates of 3-methanesulfonylpropionitrile having at least one isotope substituent (the active compound). The active compound in the pharmaceutical compositions in general is in an amount of about 0.01-20%, or 0.05-20%, or 0.1-20%, or 0.2-15%, or 0.5-10%, or 1-5% (w/w) for a topical formulation; about 0.1-5% for an injectable formulation, 0.1-5% for a patch formulation, about 1-90% for a tablet formulation, and 1-100% for a capsule formulation.

In one embodiment, the active compound is incorporated into any acceptable carrier, including creams, gels, lotions or other types of suspensions that can stabilize the active compound and deliver it to the affected area by topical applications. In another embodiment, the pharmaceutical composition can be in the dosage forms such as tablets, capsules, granules, fine granules, powders, syrups, suppositories, injectable solutions, patches, or the like. The above pharmaceutical composition can be prepared by conventional methods.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cystine, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and poloxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylene diamine tetra-acetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of the active compound of the present invention may contain other excipients that have no bioactivity and no reaction with the active compound. Excipients of a tablet may include fillers, binders, lubricants and glidants, disintegrators, wetting agents, and release rate modifiers. Binders promote the adhesion of particles of the formulation and are important for a tablet formulation. Examples of binders include, but not limited to, carboxymethylcellulose, cellulose, ethylcellulose, hydroxypropylmethylcellulose, methylcellulose, karaya gum, starch, starch, and tragacanth gum, poly(acrylic acid), and polyvinylpyrrolidone.

For example, a patch formulation of the active compound of the present invention may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethyl ether.

Topical formulations including the active compound of the present invention can be in a form of gel, cream, lotion, liquid, emulsion, ointment, spray, solution, and suspension. The inactive ingredients in the topical formulations for example include, but not limited to, lauryl lactate (emollient/permeation enhancer), diethylene glycol monoethyl ether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

In one embodiment, lauryl lactate (for example, at about 0.1-10%, or about 0.2-5%, or about 0.5-5%) is included in the topical gel formulation.

In another embodiment, diethylene glycol monoethyl ether is included in the topical gel formulation.

Method of Use

The present invention is directed to a method of treating inflammation and/or pain. The active compound deuterated 3-methanesulfonylpropionitrile can be used as is, or it can be administered in the form of a pharmaceutical composition that additionally contains a pharmaceutically acceptable carrier. The method comprises the steps of first identifying a subject suffering from inflammation and/or pain, and administering to the subject deuterated 3-methanesulfonylpropionitrile, in an amount effective to treat inflammation and/or pain. "An effective amount," as used herein, is the amount effective to treat a disease by ameliorating the pathological condition or reducing the symptoms of the disease.

In one embodiment, the method reduces or alleviates the symptoms associated with inflammation. The present invention provides a method to treat localized manifestations of inflammation characterized by acute or chronic swelling, pain, redness, increased temperature, or loss of function in some cases.

In another embodiment, the present invention provides a method to alleviate the symptoms of pain regardless of the cause of the pain. The general term "pain" treatable by the present method includes traumatic pain, neuropathic pain, organ pain, and pain associated with diseases. Traumatic pain includes pain resulting from injury, post-surgical pain and inflammatory pain. Neuropathic pain includes neuropathic and idiopathic pain syndromes, and pain associated with neuropathy such as diabetic neuropathy, causalgia, brachial plexus avulsion, occipital neuralgia, fibromyalgia, gout, and other forms of neuralgia. Organ pain includes ocular, corneal, bone, heart, skin/burn, visceral (kidney, gall bladder, etc.), joint, and muscle pain. Pain associated with diseases includes pain associated with cancer, AIDS, arthritis, herpes and migraine. The present invention reduces pain of varying severity, i.e. mild, moderate and severe pain; acute and chronic pain. The present invention is effective in treating joint pain, muscle pain, tendon pain, and burn pain.

In preferred embodiments, the present invention is useful in treating inflammation and/or pain associated in a musculoskeletal system or on the skin. The highly innervated, musculoskeletal and skin systems have a high capacity for demonstration of pain. In addition, the musculoskeletal system has a high capacity for tissue swelling, and the skin has a high capacity for redness, swelling, and heat. In musculoskeletal and skin systems, the degree of tissue damage is frequently magnified out of proportion to the resulting inflammatory response. In the skin for example, merely firm stroking will cause release of the cytokines, IL-1 and TNF.

The present invention provides a method for treating inflammation and/or pain associated with inflammatory skeletal or muscular diseases or conditions. The method comprises the steps of identifying a subject in need thereof, and administering to the subject the active compound, in an amount effective to treat inflammation and/or pain. The skeletal or muscular diseases or conditions include musculoskeletal sprains, musculoskeletal strains, tendonopathy, peripheral radiculopathy, rheumatoid arthritis, osteoarthritis, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epichondylitis (pitchers elbow) and trochanteric bursitis, temporomandibular joint syndrome, and fibromyalgia.

The present invention provides a method for treating inflammation and/or pain associated with inflammatory skin diseases such as psoriasis, acne, rosacea, and dermatitis, particularly contact dermatitis, and atopic dermatitis. The method comprises the steps of identifying a subject in need thereof, and administering to the subject the active compound, in an amount effective to treat inflammation and/or pain.

The present invention further provides a method for treating inflammatory skin diseases such as dermatitis, psoriasis, and acne (acne vulgaris). The method comprises the steps of identifying a subject in need thereof, and administering to the subject the active compound, in an amount effective to reduce or eliminate the symptoms of the disease.

Dermatitis (also called eczema) is generic inflammation of the skin. Specific types of dermatitis include atopic, contact, nummular, and photo-induced.

Contact dermatitis is a localized rash or irritation of the skin caused by contact with a foreign substance. Only the superficial regions of the skin are affected in contact dermatitis. Inflammation of the affected tissue is present in the epidermis (the outermost layer of skin) and the outer dermis (the layer beneath the epidermis). Contact dermatitis results in large, burning, and itchy rashes. Contact dermatitis is an inflammatory condition of the skin either of irritant exposure to the skin without specific adaptive immunologic pathogenesis or of allergic sensitization and subsequent exposure of the skin to the sensitizing allergen with specific adaptive immunologic pathogenesis. Both involve innate and acquired immune system response including arachidonic acid and cytokine components that initiate and propagate the disease through cell to cell messaging by eicosanoid and/or cytokine moieties produced by epidermal cells, macrophages, dendritic cells, neutrophils, eosinophils, and various T and B lymphocytes. Contact dermatitis may be either acute or chronic. The acute forms are pruritic with erythema, edema, and micro or macrovesiculation in the areas of skin contact by the initiating factor. The chronic forms are pruritic with milder erythema, scaling, lichenification, and possibly fissuring particularly on the hands.

Allergic contact dermatitis is a T cell-mediated delayed type hypersensitivity reaction that occurs upon hapten challenge in sensitized individuals. The inflammatory response in classical allergic contact dermatitis requires both a sensitization phase and an elicitation phase responsible for the recruitment and activation of specific T cells at the site of hapten skin challenge.

Atopic dermatitis is a genetically determined disease that is part of the broader disease complex of atopy that includes asthma, hay fever, and atopic dermatitis. Many individuals with atopic dermatitis have various mutations of the filaggrin gene that codes for an important epidermal structural protein that when defective, results in abnormal barrier function of the epidermis. The altered barrier allows exposure to multiple environmental allergens that are first recognized by innate immune responses involving arachidonic acid and eicosanoids and recruitment of eosinophils, mast cells, and other inflammatory cells that initiate acute responses of itch, erythema, and subsequent scratching and additionally activate the adaptive immune responses that involve inflammation by lymphocytes predominantly of a TH 2 derivation and activity. Atopic dermatitis is responsive to a number of cytokine inhibitors such as cyclosporine, and tacrolimus.

Current theory of the pathogenesis of psoriasis is that in individuals who are genetically susceptible a triggering event in the epidermis such as injury or super antigen contact initiates an response of the innate immune system with arachidonic acid and eicosanoid generation, recruitment and activity of neutrophils. Subsequent transformation of the response to that of a TH 1 adaptive immunity with cytokine activation and activity of specific T lymphocytes effect the pathological changes in the epidermis and dermis, which result in the typical psoriasis lesions of plaques that are erythematous, thickened, and scaly. Psoriasis is responsive to various immunomodulators including cyclosporine, methotrexate, and a host of specific biologicals that interfere with cytokine signaling.

Acne vulgaris, a progressively inflammatory disorder of the pilosebaceous follicular unit especially of the face and upper chest and back is a very common disease of both males and females after initiation of puberty, and in females even prior to adrenal gland maturity. Increased production of androgenic hormones by adrenal, ovarian, and testicular glands and by the pilosebaceous unit itself produce an increase in sebum and changes in its lipid composition, which combine with follicular epithelial cells to produce some degree of obstruction of the infra-infundibular portion of the pilosebaceous follicle resulting in the initial lesion of acne, the microcomedo. This consequent dilation of the pore and the changed composition of sebum at puberty facilitate colonization of the follicle by *Propionibacterium acnes* bacilli that produce enzymes to degrade the triglycerides in sebum to free fatty acids that leak through the follicle into the dermis and incite arachidonic acid pathways of eicosanoid production and subsequent initiation of inflammation. The bacilli also initiate chemokine production that attracts further inflammatory cells to the area and consequent cytokine production and action to continue and amplify inflammation. The initiation and propagation of progressive inflammation in the microcomedo produces the evolution to the several hallmark lesions of inflammatory acne, papule, pustule, nodule, and cyst. The present invention is useful to treat common acne, comedonic acne, papulopustular acne, papulocomedonic acne, nodulocystic acne, acne conglobata, cheloid acne of the nape of the neck, recurrent miliary acne, necrotic acne, neonatal acne, occupational acne, acne rosacea, senile acne, solar acne or acne medicamentosa.

Rosacea is a chronic condition characterized by facial erythema and sometimes pimples. Rosacea typically begins as redness on the central face across the cheeks, nose, or forehead, but can also less commonly affect the neck, chest, ears, and scalp. In some cases, additional symptoms, such as semi-permanent redness, telangiectasia (dilation of superficial blood vessels on the face), red domed papules (small bumps) and pustules, red gritty eyes, burning and stinging sensations, and in some advanced cases, a red lobulated nose (rhinophyma), may develop. There are 3 subtypes of rosacea that affect the skin: erythematotelangiectatic rosacea, papulopustular rosacea, and phymatous rosacea.

Deuterated 3-methanesulfonylpropionitriles are effective to treat inflammation and/or pain associated with psoriasis, acne, rosacea, and dermatitis, such as contact dermatitis, and atopic dermatitis.

Deuterated 3-methanesulfonylpropionitriles are effective to treat inflammatory skin diseases such as dermatitis (atopic dermatitis), psoriasis, acne, and rosacea.

Deuterated 3-methanesulfonylpropionitriles are effective in treating atopic dermatitis and alleviating one or more symptoms selected from the group consisting of erythema, induration, lichenification, scaling, and oozing and crusting. Deuterated 3-methanesulfonylpropionitriles are effective in treating psoriasis and alleviating erythema, scaling, and/or thickness of the psoriasis lesions. Deuterated 3-methanesulfonylpropionitriles are effective in treating acne and alleviating acne lesions selected from the groups consisting of closed comedones, papules, pustules, nodules, and cysts.

Deuterated 3-methanesulfonylpropionitriles are effective in treating rosacea and alleviating one or more symptoms selected from the group consisting of erythema, telangiectasia, red domed papules and pustules, red gritty eyes, and burning and stinging sensations.

The pharmaceutical composition of the present invention can be applied by local administration and systemic administration. Local administration includes topical administration. Systemic administration includes oral, parenteral (such as intravenous, intramuscular, subcutaneous or rectal), and other systemic routes of administration. In systemic administration, the active compound first reaches plasma and then distributes into target tissues. Topical administration and oral administration are preferred routes of administration for the present invention.

Dosing of the composition can vary based on the extent of the injury and each patient's individual response. For systemic administration, plasma concentrations of active compounds delivered can vary; but are generally $1\times10^{-10}$-$1\times10^{-4}$ moles/liter, and preferably $1\times10^{-8}$-$1\times10^{-5}$ moles/liter.

In one embodiment, the composition is applied topically onto the affected area and rubbed into it. The composition is topically applied at least one or two times a day, or 3 to 4 times per day, depending on the medical issue and the disease pathology being chronic or acute. In general, the topical composition comprises about 0.01-20%, or 0.05-20%, or 0.1-20%, or 0.2-15%, 0.5-10, or 1-5% (w/w) of the active compound. For example, the topical composition comprises about 1 or 5% (w/w) of the active compound. Depending on the size of the affected area, 0.2-85 mL, typically 0.2-10 mL, of the topical composition is applied to the individual per dose. The active compound passes through skin and is delivered to the site of discomfort.

In one embodiment, the pharmaceutical composition is administrated orally to the subject. The dosage for oral administration is generally 1-50, and preferably 1-5 mg/kg/day.

In one embodiment, the pharmaceutical composition is administrated subcutaneously to the subject. The dosage for subcutaneous administration is generally 0.3-20, and preferably 0.3-3 mg/kg/day.

Those of skill in the art will recognize that a wide variety of delivery mechanisms are also suitable for the present invention.

The present invention is useful in treating a mammal subject, such as humans, horses, and dogs. The present invention is particularly useful in treating humans.

The following examples further illustrate the present invention. These examples are intended merely to be illustrative of the present invention and are not to be construed as being limiting.

EXAMPLES

Example 1. Preparation of 3-Methanesulfonylpropionitrile-d$_3$

The title compound (3) was prepared as shown in Scheme 3. Treatment of 3-bromopropionitrile (1) with an aqueous solution of sodium hydrosulfide (NaSH) gave the corresponding thiol, which was alkylated with iodomethane-d$_3$ under basic conditions. The resultant sulfide (2) was oxidized to the target sulfone with hydrogen peroxide.

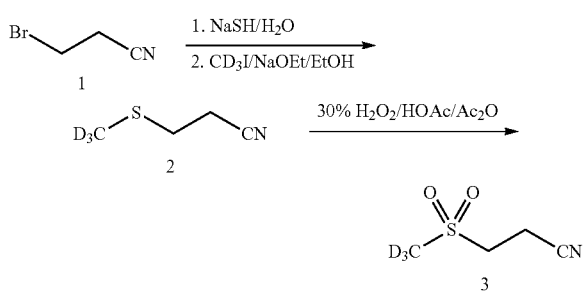

3-(trideuteriomethyl)sulfonylpropionitrile (3)

Sulfide 2 (34.3 mmol) was transferred to a 100 mL 3N RB flask containing a stir bar, followed by HOAc (13 mL) and an equal volume of Ac$_2$O. The flask was equipped with a thermocouple, addition funnel, and stopper and placed in an ice bath. The funnel was charged with 30% H$_2$O$_2$ (13 mL), which was added dropwise over 2 h such that an internal temperature of <32° C. was maintained. After cooling, stirring was stopped and the mixture stood ON at ambient temperature. The reaction mixture was concentrated to a clear, colorless liquid that was seeded with a single crystal of product from a previous run. After ~2 h, the resultant crystalline mass was cooled with dry ice, triturated with cold EtOH, collected by vacuum filtration, washed with cold EtOH and air-dried: 2.24 g, white crystalline solid (48%); 98.3% (GC-FID); m/z 136 (GC-MS/MS); mp 69-73° C.; $^1$H NMR (CD$_3$OD; 400 MHz): δ 2.991 [t, 2H, C$\underline{H}_2$CN, J (Hz) 7.10, 7.27], 3.486 [t, 2H, C$\underline{H}_2$SO$_2$, J (Hz) 7.10, 7.26]; $^{13}$C NMR (CD$_3$OD; 100 MHz): 118.69 ppm, 50.23 ppm, 40.42 ppm, 12.08 ppm; FTIR-ATR: 2253 cm$^{-1}$ (CN); 1277 cm$^{-1}$ (SO$_2$); 1127 cm$^{-1}$ (SO$_2$); Calculated for C$_4$H$_4$D$_3$NO$_2$S (FW 136.19): C, 35.27; H, 5.18 [H+D as H=H$_7$=(1.008×7)/136.19=5.18]; N, 10.29; S, 23.55. Found: C, 35.31; H, 5.19; N, 10.28; S, 23.52;

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A compound of 3-methanesulfonylpropionitrile or a pharmaceutically acceptable solvate thereof, in which at least one of the hydrogens is substituted with $^2$H (deuterium).

2. The compound according to claim 1, which is

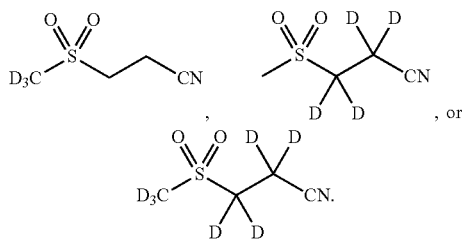

wherein D represents deuterium.

3. The compound according to claim 2, which is

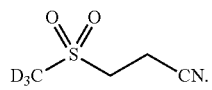

4. The compound according to claim 2, which is

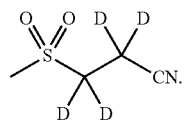

5. The compound according to claim 2, which is

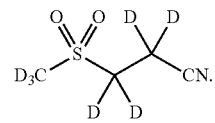

6. A method for preparing the compound of claim 3, comprising:
   reacting 3-bromopropionitrile with an aqueous solution comprising sodium hydrosulfide (NaSH) to form a thiol,
   alkylating the thiol with trideuterated-iodomethane under a basic condition to form a sulfide, and
   oxidizing the sulfide with hydrogen peroxide to form the compound of claim 3.

7. A method for preparing the compound of claim 4, comprising:
   protecting 2-bromoethanol-1,1,2,2-d$_4$ with a protecting group,
   alkylating sodium methylsulfinate with the protected 2-bromoethanol-1,1,2,2-d$_4$ to form a sulfone,
   removing the protected group in the sulfone by an acidic condition,
   converting the de-protected sulfone to a tosylate, and
   reacting the tosylate with a cyanide ion to produce the compound of claim 4.

8. A method for preparing the compound of claim 5, comprising:
   protecting 2-bromoethanol-1,1,2,2-d$_4$ with a protecting group,
   reacting the protected 2-bromoethanol-1,1,2,2-d$_4$ with an aqueous solution comprising sodium hydrosulfide (NaSH) to form a thiol,
   alkylating the thiol with trideuterated-iodomethane under a basic condition to form a sulfide,
   oxidizing the sulfide with hydrogen peroxide to form a sulfone,
   removing the protected group in the sulfone by an acidic condition,
   converting the de-protected sulfone to a tosylate, and
   reacting the tosylate with a cyanide ion to produce the compound of claim 5.

* * * * *